(12) United States Patent
Pillai (10) Patent No.: US 11,376,403 B2
(45) Date of Patent: Jul. 5, 2022

(54) TRANSVASCULAR ACCESS METHODS

(71) Applicant: Vascular Access Technologies, Inc., South Jordan, UT (US)

(72) Inventor: Lakshmikumar Pillai, Morgantown, WV (US)

(73) Assignee: Vascular Access Technologies, Inc., South Jordan, UT (US)

( * ) Notice: Subject to any disclaimer, the term of this patent is extended or adjusted under 35 U.S.C. 154(b) by 330 days.

(21) Appl. No.: 16/503,983

(22) Filed: Jul. 5, 2019

(65) Prior Publication Data

US 2019/0321600 A1    Oct. 24, 2019

Related U.S. Application Data

(62) Division of application No. 15/464,055, filed on Mar. 20, 2017, now Pat. No. 10,342,956, which is a
(Continued)

(51) Int. Cl.
| | | |
|---|---|---|
| A61M 25/06 | (2006.01) | |
| A61M 1/36 | (2006.01) | |
| A61M 27/00 | (2006.01) | |
| A61B 17/11 | (2006.01) | |
| A61M 60/148 | (2021.01) | |

(52) U.S. Cl.
CPC .. *A61M 25/0606* (2013.01); *A61B 2017/1107* (2013.01); *A61B 2017/1139* (2013.01); *A61M 1/3653* (2013.01); *A61M 1/3655* (2013.01); *A61M 1/3659* (2014.02); *A61M 27/002* (2013.01); *A61M 60/148* (2021.01)

(58) Field of Classification Search
CPC ............ A61M 25/0606; A61M 60/148; A61M 27/002; A61M 1/3659; A61M 1/3653; A61M 1/3655; A61B 2017/1107; A61B 2017/1139
See application file for complete search history.

(56) References Cited

U.S. PATENT DOCUMENTS

| | | |
|---|---|---|
| 4,559,039 A | 12/1985 | Ash et al. |
| 4,790,825 A | 12/1988 | Bernstein et al. |
| (Continued) | | |

FOREIGN PATENT DOCUMENTS

| | | |
|---|---|---|
| WO | 2004018029 | 3/2004 |
| WO | 2005053547 | 6/2005 |
| (Continued) | | |

OTHER PUBLICATIONS

Office Action dated Apr. 13, 2020 for U.S. Appl. No. 15/834,998.
(Continued)

*Primary Examiner* — Theodore J Stigell
(74) *Attorney, Agent, or Firm* — Dorsey & Whitney LLP (57) ABSTRACT

Various methods employing transvascular access devices are described, including a method of placing a central catheter in a peripheral vein in an arm of a patient; a method of providing percutaneous access to the heart of a patient; a method of clearing a clotted arteriovenous dialysis graft; a method of creating multiple access points into a single blood vessel; a method of creating an AV fistula in a patient; and a method of providing a bypass to a blockage in a popliteal artery in a patient.

19 Claims, 5 Drawing Sheets

Related U.S. Application Data division of application No. 13/904,876, filed on May 29, 2013, now Pat. No. 9,623,217.

(60) Provisional application No. 61/653,303, filed on May 30, 2012.

(56) References Cited

U.S. PATENT DOCUMENTS

| | | | |
|---|---|---|---|
| 4,966,163 A | 10/1990 | Kraus et al. | |
| 5,421,348 A | 6/1995 | Larnard | |
| 5,492,530 A | 2/1996 | Fischell et al. | |
| 5,685,820 A | 11/1997 | Riek et al. | |
| 5,733,248 A | 3/1998 | Adams et al. | |
| 6,047,700 A | 4/2000 | Eggers et al. | |
| 6,102,926 A | 8/2000 | Tartaglia et al. | |
| 6,190,353 B1 | 2/2001 | Makower et al. | |
| 6,217,527 B1 | 4/2001 | Selmon et al. | |
| 6,475,226 B1 | 11/2002 | Belef et al. | |
| 6,485,513 B1 | 11/2002 | Fan | |
| 6,508,777 B1 | 1/2003 | Macoviak et al. | |
| 6,554,794 B1 | 4/2003 | Mueller et al. | |
| 6,623,480 B1 | 9/2003 | Kuo et al. | |
| 6,709,444 B1 | 3/2004 | Makower | |
| 6,726,677 B1 | 4/2004 | Flaherty et al. | |
| 6,955,657 B1 | 10/2005 | Webler | |
| 7,008,979 B2 | 3/2006 | Schottman et al. | |
| 7,374,567 B2 | 5/2008 | Heuser | |
| 7,648,517 B2 | 1/2010 | Makower et al. | |
| 8,019,420 B2 | 9/2011 | Hine et al. | |
| 8,241,311 B2 | 8/2012 | Ward et al. | |
| 8,374,680 B2 | 2/2013 | Thompson | |
| 8,409,236 B2* | 4/2013 | Pillai | A61B 17/3403 606/185 |
| 8,568,435 B2 | 10/2013 | Pillai et al. | |
| 9,220,874 B2 | 12/2015 | Pillai et al. | |
| 9,282,967 B2 | 3/2016 | Paris et al. | |
| 2001/0012924 A1 | 8/2001 | Milo et al. | |
| 2001/0023346 A1 | 9/2001 | Loeb | |
| 2002/0004666 A1 | 1/2002 | Schwager et al. | |
| 2002/0029060 A1 | 3/2002 | Hogendijk et al. | |
| 2002/0120250 A1 | 8/2002 | Altman | |
| 2002/0122877 A1 | 9/2002 | Harish et al. | |
| 2002/0133168 A1 | 9/2002 | Smedley et al. | |
| 2002/0169377 A1 | 11/2002 | Khairkhahan et al. | |
| 2003/0040771 A1 | 2/2003 | Hyodoh | |
| 2004/0039371 A1 | 2/2004 | Tockman et al. | |
| 2004/0059280 A1 | 3/2004 | Makower et al. | |
| 2004/0082850 A1 | 4/2004 | Bonner et al. | |
| 2004/0097880 A1* | 5/2004 | Schur | A61M 25/007 604/164.01 |
| 2004/0133168 A1 | 7/2004 | Salcudean et al. | |
| 2004/0181150 A1 | 9/2004 | Evans et al. | |
| 2004/0181238 A1 | 9/2004 | Zarbatany et al. | |
| 2005/0101984 A1 | 5/2005 | Chanduszko et al. | |
| 2005/0149097 A1 | 7/2005 | Regnell et al. | |
| 2005/0209579 A1 | 9/2005 | Yacoubian et al. | |
| 2006/0009737 A1 | 1/2006 | Whiting et al. | |
| 2006/0135962 A1 | 6/2006 | Kick et al. | |
| 2006/0173440 A1 | 8/2006 | Lamson | |
| 2006/0247750 A1 | 11/2006 | Seifert et al. | |
| 2007/0021767 A1 | 1/2007 | Breznock | |
| 2007/0203515 A1 | 3/2007 | Heuser et al. | |
| 2008/0082136 A1 | 4/2008 | Gaudini | |
| 2008/0125748 A1 | 5/2008 | Patel | |
| 2008/0154172 A1 | 6/2008 | Mauch | |
| 2008/0171944 A1 | 7/2008 | Brenneman et al. | |
| 2008/0215008 A1 | 9/2008 | Nance et al. | |
| 2008/0249565 A1 | 10/2008 | Michler et al. | |
| 2009/0112050 A1 | 4/2009 | Farnan et al. | |
| 2009/0240122 A1 | 9/2009 | Avitsian | |
| 2010/0249491 A1 | 9/2010 | Farnan et al. | |
| 2011/0178530 A1 | 7/2011 | Bly | |
| 2011/0295206 A1* | 12/2011 | Gurley | A61B 6/12 604/164.1 |
| 2012/0136247 A1 | 5/2012 | Pillai | |
| 2012/0136366 A1 | 5/2012 | Pillai | |
| 2013/0006282 A1 | 1/2013 | Wilkinson | |
| 2013/0072957 A1 | 3/2013 | Anderson | |
| 2013/0324901 A1 | 12/2013 | Pillai | |
| 2013/0324967 A1 | 12/2013 | Pillai et al. | |
| 2014/0018837 A1 | 1/2014 | Zhou et al. | |
| 2014/0142418 A1 | 5/2014 | Gurley et al. | |
| 2014/0142677 A1 | 5/2014 | Heuser et al. | |
| 2015/0320357 A1 | 11/2015 | Kauaguntla et al. | |
| 2017/0035591 A1 | 2/2017 | De Pablo et al. | |
| 2017/0056625 A1 | 3/2017 | Pillai | |
| 2020/0069919 A1 | 3/2020 | Pillai | |
| 2020/0338320 A1 | 10/2020 | Pillai | |

FOREIGN PATENT DOCUMENTS

| | | |
|---|---|---|
| WO | 2011068540 | 6/2011 |
| WO | 2013119547 | 8/2013 |

OTHER PUBLICATIONS

Notice of Allowance dated Feb. 5, 2020 for U.S. Appl. No. 15/835,114.
Notice of Allowance dated Jan. 28, 2019 for U.S. Appl. No. 14/949,243.
Notice of Allowance dated Mar. 19, 2019 for U.S. Appl. No. 15/464,055.
Notice of Allowance dated May 1, 2019 for U.S. Appl. No. 15/347,478.
Office Action dated Jan. 30, 2018 for U.S. Appl. No. 14/949,243.
Office Action dated May 30, 2017 for U.S. Appl. No. 14/949,243.
Office Action dated Jun. 14, 2018 for U.S. Appl. No. 14/949,243.
Office Action dated Aug. 29, 2019 for U.S. Appl. No. 15/835,114.
Office Action dated Sep. 7, 2018 for U.S. Appl. No. 15/347,478.
Office Action dated Sep. 27, 2018 for U.S. Appl. No. 15/464,055.
Office Action dated Oct. 2, 2018 for U.S. Appl. No. 14/949,243.
Faul, et al., Vascular Disease Management, vol. 5 No. 5 ,Sep./Oct. 2008 ,128-133.
Huang, et al., Evaluation of the Needle Technique for Producing an Arteriovenous Fistula, Journal of Applied Physiology, vol. 77(6), Dec. 1994 ,2907-2911.
Khanna, et al., sharpening of Hollow Silicon Microneedles to Reduce Skin Penetration Force, ,Mar. 15, 2010 ,045011.
Lumend Inc., et al., Outback LTD Re-Entry Catheter; Product Resources (http://www.lumend.com/Images/Technology/Products/brochure.pdf), ,Jul. 19, 2006.
Mewissen, et al., Revascularization of Long FP Arterial Occlusions, Endovascular Today ,Mar. 2004 ,2-4.
O'Callaghan, et al., Dynamics of Stab Wounds: Force Required for Penetration of Various Cadaveric Himan Tissues, Forensic Sci. Int'l., vol. 104 ,Oct. 11, 1999 ,173-178.
Office Action dated Feb. 2, 2021 for U.S. Appl. No. 15/855,672.
Office Action dated Feb. 3, 2021 for U.S. Appl. No. 15/834,998.
Office Action dated Sep. 24, 2020 for U.S. Appl. No. 15/834,998.
Office Action dated May 25, 2021 for U.S. Appl. No. 15/834,998.
Office Action dated Jun. 22, 2021 for U.S. Appl. No. 15/855,672.
Office Action dated Oct. 23, 2019 for U.S. Appl. No. 15/834,998.
Office Action dated Oct. 1, 2021 for U.S. Appl. No. 15/855,672.

* cited by examiner

```
┌─────────────────────────────────────────────────────────────┐
│ Inserting an access device percutaneously through an entry  │
│ site in a femoral artery of the patient, the access device  │
│ comprising a vascular catheter                              │
└─────────────────────────────────────────────────────────────┘
                              │
┌─────────────────────────────────────────────────────────────┐
│ Advancing a distal end of the vascular catheter from the    │
│ entry site to an exit site in an axillary artery of the     │
│ patient                                                     │
└─────────────────────────────────────────────────────────────┘
                              │
┌─────────────────────────────────────────────────────────────┐
│ Advancing a puncture tool from the distal end of the        │
│ catheter through the axillary artery wall and skin of the   │
│ patient at the exit site                                    │
└─────────────────────────────────────────────────────────────┘
                              │
┌─────────────────────────────────────────────────────────────┐
│ After the step of advancing the puncture tool, inserting a  │
│ cardiac access catheter into the axillary artery at the     │
│ exit site                                                   │
└─────────────────────────────────────────────────────────────┘
                              │
┌─────────────────────────────────────────────────────────────┐
│ Advancing the cardiac access catheter through the axillary  │
│ artery, subclavian artery and the aorta to the patient's    │
│ heart                                                       │
└─────────────────────────────────────────────────────────────┘
                              │
┌─────────────────────────────────────────────────────────────┐
│ Performing transcatheter aortic valve implantation or       │
│ implanting a left ventricular assist device                 │
└─────────────────────────────────────────────────────────────┘
```

FIG. 5

TRANSVASCULAR ACCESS METHODS

CROSS REFERENCE TO RELATED APPLICATIONS

This application is a divisional of U.S. application Ser. No. 15/464,055, filed Mar. 20, 2017, now U.S. Pat. No. 10,342,956, which is a divisional of U.S. application Ser. No. 13/904,876, filed May 29, 2013, now U.S. Pat. No. 9,623,217, which application claims the benefit of U.S. Application No. 61/653,303, filed May 30, 2012, the disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The present invention relates to methods and devices for providing transvascular access to blood vessels. Prior devices and methods have been described for providing, e.g., access for placing a central venous line in the jugular vein using a remote vascular entry point, such as the femoral vein. In those prior approaches, a steerable catheter with a bent or bendable tip is guided from the femoral or other entry point to the desired central venous line entry point in the jugular vein. The tip of a sharp wire or stylet is then advanced out of the catheter and through the vessel wall and skin of the patient, and the central venous line is then inserted over the wire or stylet. More details of these prior devices and methods may be found in U.S. Application No. 61/653,182 (filed May 30, 2012); application Ser. No. 12/861,716 (filed Aug. 23, 2010), now U.S. Pat. No. 8,409, 236; U.S. application Ser. No. 12/366,517 (filed Feb. 5, 2009); and U.S. application Ser. No. 11/424,131 (filed Jun. 14, 2006), the disclosures of which are incorporated herein by reference.

SUMMARY OF THE DISCLOSURE

The present invention relates to methods for providing transvascular access to intravascular or intracardiac locations.

One aspect of the invention provides a method of placing a central catheter in a peripheral vein in an arm of a patient, such as a cephalic vein, a basilic vein or a brachial vein. The method includes the steps of inserting an access device percutaneously through an entry site in a femoral vein of the patient, the access device comprising a vascular catheter; advancing a distal end of the vascular catheter from the entry site to an exit site in the peripheral vein; advancing a puncture tool from the distal end of the catheter through the peripheral vein wall and skin of the patient at the exit site; and after the step of advancing the puncture tool, inserting the central catheter into the peripheral vein at the exit site.

Another aspect of the invention provides a method of providing percutaneous access to the heart of a patient. The method includes the steps of inserting an access device percutaneously through an entry site in a femoral artery of the patient, the access device comprising a vascular catheter; advancing a distal end of the vascular catheter from the entry site to an exit site in an axillary artery of the patient; advancing a puncture tool from the distal end of the catheter through the axillary artery wall and skin of the patient at the exit site; after the step of advancing the puncture tool, inserting a cardiac access catheter into the axillary artery at the exit site; and advancing the cardiac access catheter through the axillary artery, subclavian artery and the aorta to the patient's heart to, e.g., perform transcatheter aortic valve implantation or implant a left ventricular assist device.

Still another aspect of the invention provides a method of clearing a clotted arteriovenous dialysis graft. The method includes the steps of inserting an access device into the graft at a first access point (e.g., above an arterial anastomosis), the access device comprising a vascular catheter; advancing a distal end of the vascular catheter from the first access point through the graft to a second access point in the graft (e.g., in front of a venous graft anastomosis); advancing a puncture tool from the distal end of the catheter through the graft wall at the second access point; and inserting a clot clearing device into the graft at the second access point.

Another aspect of the invention provides a method of creating multiple access points into a single blood vessel. The method includes the steps of inserting an access device percutaneously into the vessel through a first access point, the access device comprising a vascular catheter; advancing a distal end of the vascular catheter from the first access point through the vessel to a second access point; advancing a puncture tool from the distal end of the catheter through the vessel wall and skin of the patient at the second access point; inserting a catheter or device into the vessel at the second access point; removing the access device from the vessel; and inserting another catheter or device into the vessel at the first access point.

Yet another aspect of the invention provides a method of creating an AV fistula in a patient. The method includes the steps of inserting an access device into the patient's femoral artery, the access device comprising a vascular catheter; advancing a distal end of the vascular catheter to a fistula site within the axillary artery; advancing a puncture tool from the distal end of the catheter through the axillary artery wall into the axillary vein to form a fistula between the axillary artery and the axillary vein; and inserting a covered stent into the fistula. In some embodiments, the method also includes before the step of inserting the covered stent, expanding the size of the fistula. In some embodiments the method also includes the step of inserting an intravascular ultrasound device into the femoral vein and advancing the intravascular ultrasound device to a position in the axillary vein adjacent to the vascular catheter.

Still another aspect of the invention provides a method of providing a bypass to a blockage in a popliteal artery in a patient. The method includes the steps of inserting a first access device into the patient's femoral artery at a first entry point, the first access device comprising a vascular catheter; advancing a distal end of the first access device vascular catheter to a first exit point upstream of the blockage; advancing a puncture tool from the distal end of the first access device vascular catheter through the arterial wall at the first exit point; inserting a second access device into the patient's tibial artery at a second entry point, the second access device comprising a vascular catheter; advancing a distal end of the second access device vascular catheter to a second exit point downstream of the blockage; advancing a puncture tool from the distal end of the second access device vascular catheter through the arterial wall at the second exit point; forming a subcutaneous tunnel between the first exit point and the second exit point; extending a guidewire between the first entry point and the second entry point; and delivering a bypass graft along the guidewire to extend between the first exit point and the second exit point. The some embodiments, the method also includes the step of making an incision through the patient's skin at the first exit point prior to the step of advancing the puncture tool from the distal end of the first access device vascular catheter through the arterial wall at the first exit point.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The devices and methods described in the patent applications listed above form the basis for improving some existing procedures and for performing entirely new procedures. Some of these medical methods are described below.

Placement of a Peripherally Inserted Central Catheter

Figure 1:
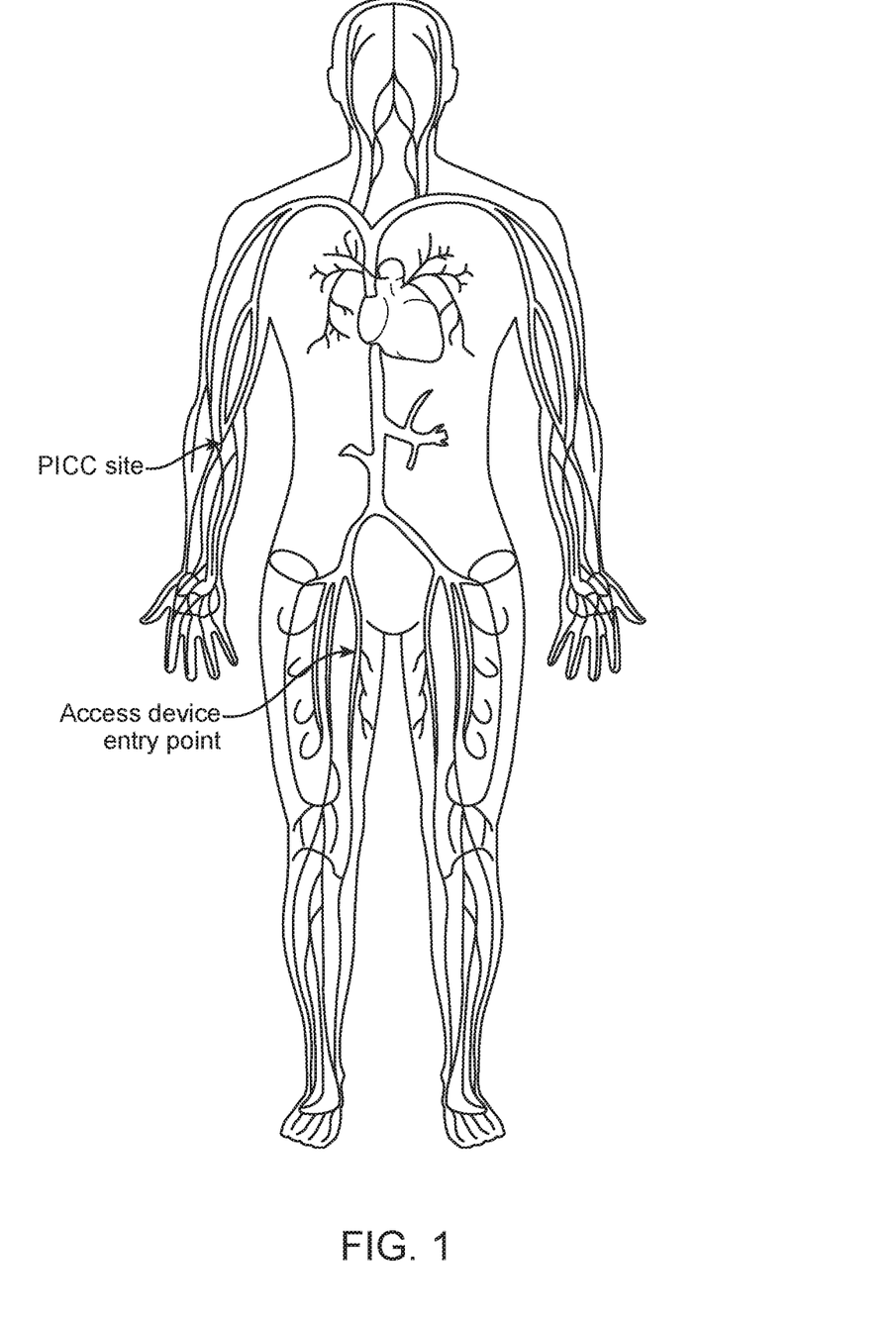
FIG. 1 shows possible entry points for a transvascular access device and a peripherally inserted central catheter according to one method of this invention.

A peripherally inserted central catheter (PICC) is a form of intravenous access typically used for patients who require intravenous delivery of a drug or nutrition over an extended period of time. The devices described in U.S. Application No. 61/653,182; U.S. Pat. No. 8,409,236; U.S. application Ser. No. 12/366,517; and U.S. application Ser. No. 11/424,131 can be used to facilitate placement of a PICC. The device may be inserted as described in these patent applications, then advanced to a site in, e.g., the cephalic vein, basilic vein or brachial vein, and the device's puncture tool (e.g., sharp stylet or needle-tipped guidewire) can be passed through the vein wall and skin to create the PICC entry point, as shown in FIG. 1. After optionally using a micropuncture catheter at the new entry point, the PICC can then be advanced into the vein.

Peripheral Artery Access for Percutaneous Retrograde Access of the Heart

Certain minimally invasive cardiac procedures require retrograde access of the heart. For example, transcatheter aortic valve implantation (TAVI) can be performed using catheters inserted into the axillary artery and advanced to the heart. As another example, left ventricular assist devices can be implanted using catheters inserted into the axillary artery and advanced to the heart.

Figure 5:
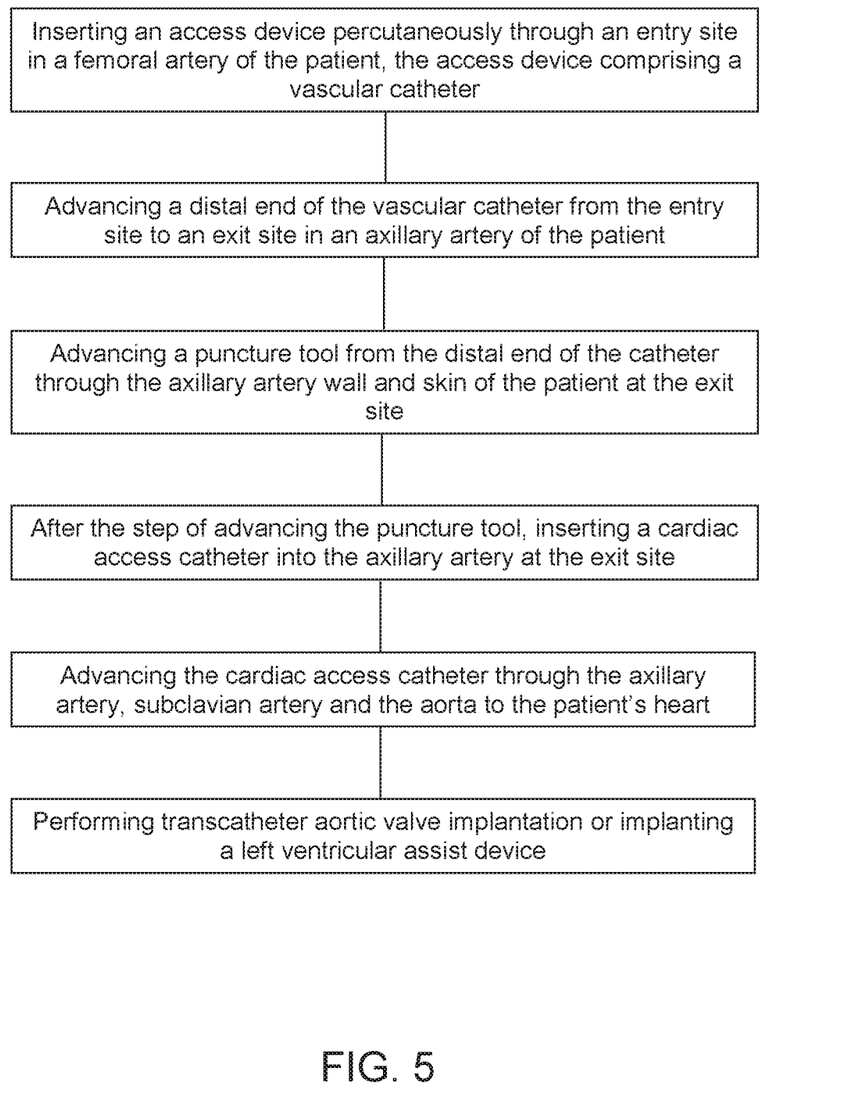
FIG. 5 illustrates steps of a method of implanting a transcatheter valve or a left ventricular assist device.

The invention includes use of devices described in U.S. Application No. 61/653,182; U.S. Pat. No. 8,409,236; U.S. application Ser. No. 12/366,517; and U.S. application Ser. No. 11/424,131 to create the arterial access for procedures performed in or around the heart. Referring to FIG. 5, the device may be inserted into the femoral artery and advanced to the desired entry point in the axillary artery (or other great artery of the head and neck, such as the carotid or subclavian arteries). The device's puncture tool (e.g., sharp stylet or needle-tipped guidewire) can be passed through the arterial wall and skin at an exit site to create the new catheter entry point. After optionally using a micropuncture catheter at the new entry point, the opening (arteriotomy) can be enlarged to the desired size, and the catheter can then be inserted into the axillary artery and advanced to the heart through the subclavian artery and aorta to perform the desired implant or other procedure. Access directly to a carotid artery or subclavian artery can also be provided in the same manner.

Treatment of Clotted Dialysis AV Graft

Hemodialysis often requires access to an autologous arteriovenous (AV) fistula formed by connecting an artery with a nearby vein. AV grafts are often used for dialysis patients who are not good candidates for an AV fistula. The AV graft is a tube formed from polyester or other biocompatible material that extends from a vein to an artery, often forming a loop in between. An AV graft may be placed, e.g., between the brachial artery and the antecubital vein, between the radial artery and the antecubital vein, between the brachial artery and the axillary vein, or between the axillary artery and the axillary vein.

AV grafts can become occluded by clotted blood. Since there is no blood flow, it can be very difficult to puncture a clotted graft from the outside and place a vascular sheath in the collapsed lumen. The invention therefore includes methods and devices for clearing AV graft clots in, e.g., an upper arm or forearm AV graft.

Figure 2:
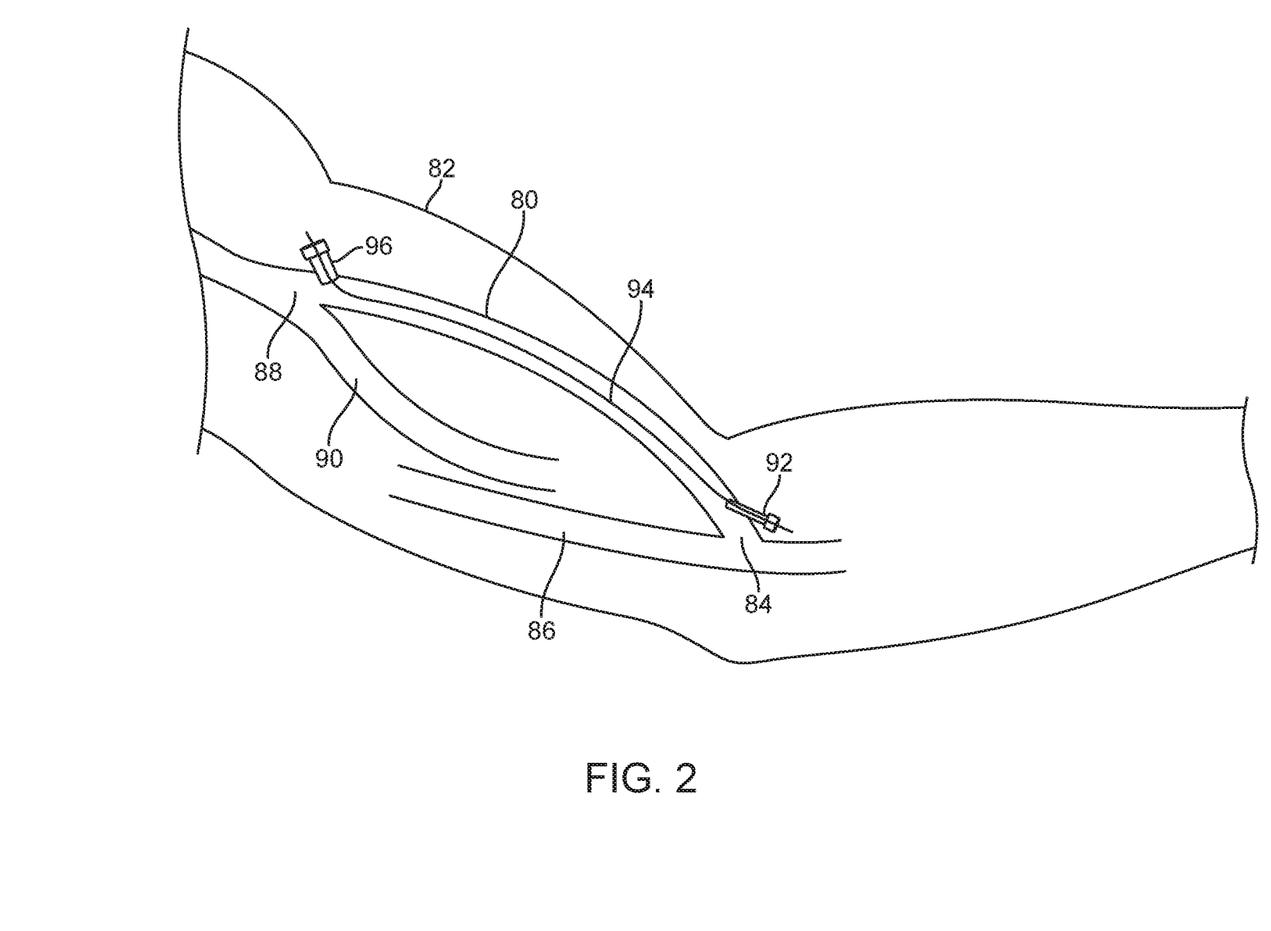
FIG. 2 illustrates a method for clearing a clotted dialysis graft according to an aspect of this invention.

FIG. 2 shows how a vascular access device can be used to clear a clotted dialysis graft. As shown, an AV graft 80 is disposed in the patient's arm 82 extending from an arterial anastomosis 84 in the brachial artery 86 to a venous anastomosis 88 in the axillary vein 90. To clear the clot, the graft 80 can be percutaneously punctured just above its arterial anastomosis 84 with an 18 gauge entry needle aimed toward the venous graft anastomosis 88 and a 6F standard vascular sheath 92 can be inserted. The venous limb and venous anastomosis 88 of the graft 80 can be declotted in the usual fashion with a suction-aspiration device (e.g., AngioJet®), and a balloon angioplasty of the venous anastomosis 88 can be performed. Then, using a device somewhat shorter than that described, e.g., in U.S. Application No. 61/653,182; U.S. Pat. No. 8,409,236; U.S. application Ser. No. 12/366,517; or U.S. application Ser. No. 11/424,131, pass the device through the vascular sheath 92 and fire the stylet out of the graft 80 to puncture through the vessel and skin just in front of the venous graft anastomosis 88. The device's stylet may then be retracted and, using a micro-puncture catheter, a 0.035" wire 94 may be inserted into the new opening. A second 6F vascular sheath 96 may then be placed over the wire. Through this new sheath the arterial anastomosis may be re-opened in the usual fashion with the AngioJet® catheter and over the wire Fogarty balloon. The sheaths may now be removed as the graft has now been declotted and is ready for dialysis access. This approach is particularly advantageous when declotting upper arm AV grafts; trying to puncture the graft just below the venous anastomosis (which is usually in the axilla-armpit) can be a challenge ergonomically, especially with the x-ray imager (C-arm) being in the way.

This approach can also be used with other vascular-based procedures requiring multiple openings in a vessel, such as ICD or pacemaker lead placement.

Creation of Multiple Access Openings in a Single Vessel

There are many procedures requiring the creation of multiple entry points into a single blood vessel for, e.g., the insertion of multiple devices into the vessel. For example, Tesio® long term hemodialysis catheters require two openings, one for each of the two free floating lumens. These catheters are typically placed in the jugular vein or subclavian vein approximately 8 mm apart. As another example, up to four electrophysiology catheters may be inserted into adjacent portions of a femoral vein and advanced to the patient's heart for electrophysiology studies or for cardiac ablation procedures. As yet another example, when implanting leads for pacemakers or implantable cardioverter/defibrillators (ICDs), multiple contiguous punctures often need to be made along the access vein (e.g., subclavian vein). Other procedures require multiple punctures and insertions in the same veins or arteries.

Veins can go into spasm after a first puncture, making subsequent punctures difficult. The device described in, e.g., U.S. Application No. 61/653,182; U.S. Pat. No. 8,409,236; U.S. application Ser. No. 12/366,517; or U.S. application Ser. No. 11/424,131 can be used to create the second and subsequent openings in the vessel followed by insertion of the second and subsequent catheters. Specifically, the device can be inserted into the first entry point in the vessel, then advanced to the second desired entry point. The device's puncture tool (e.g., sharp stylet or needle-tipped guidewire) can then be passed through the vein wall and skin to create the second entry point. After optionally using a micropuncture catheter at the new entry point, one of the catheters can then be inserted into the vessel at this second entry point while another of the catheters can be inserted at the first entry point after removal of the transvascular device.

Creation of AV Fistula for Hemodialysis

Hemodialysis often requires access to an autologous arterial/venous (AV) fistula formed by connecting an artery with a nearby vein. For example, an anastomosis can be formed between the cephalic vein and the radial artery up near the patient's wrist, between the perforating branch of the cephalic vein and proximal radial artery in the patient's forearm, between the median antecubital vein and proximal radial artery in the patient's forearm, between the brachial artery and cephalic vein further up the patient's arm, etc.

Figure 3:
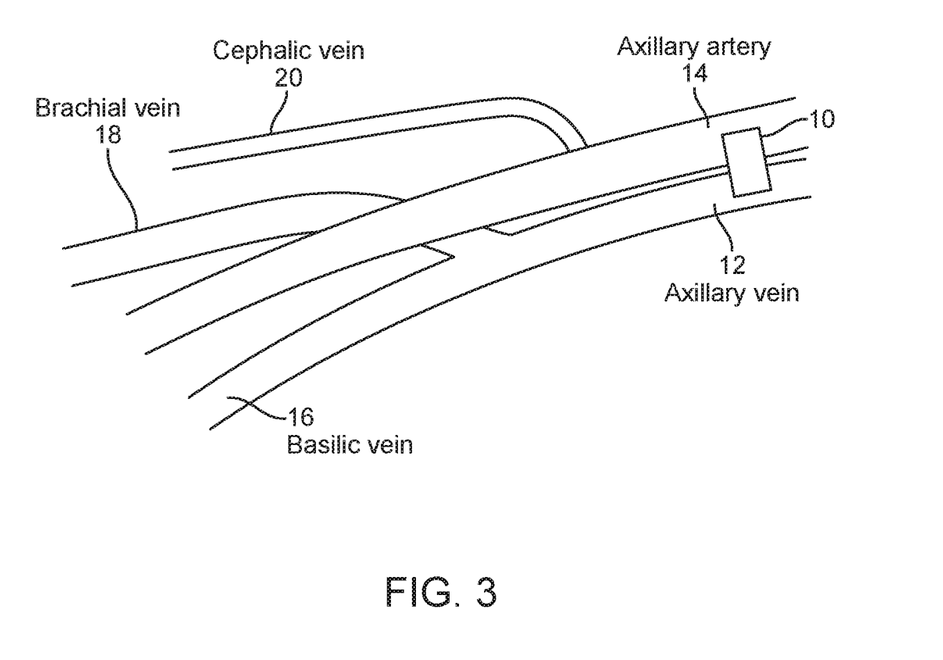
FIG. 3 illustrates creation of an arterial/venous fistula according to an aspect of this invention.

While forearm or upper arm access sites are useful for hemodialysis, AV fistulas in the arm are often not viable for very long due to clotting, fibrosis, etc. As an alternative, the device described in, e.g., U.S. Application No. 61/653,182; U.S. Pat. No. 8,409,236; U.S. application Ser. No. 12/366,517; or U.S. application Ser. No. 11/424,131 can be used to create a longer lasting fistula remote from the access site. FIG. 3 shows schematically an AV fistula 10 created between the axillary vein 12 and the axillary artery 14. These vessels are disposed adjacent to each near the shoulder. The axillary vein drains the basilic vein 16, the brachial vein 18 and the cephalic vein 20.

To create the fistula 10, a device is inserted percutaneously into the femoral artery advanced over a guidewire to the desired position in the axillary artery. An intravascular ultrasound (IVUS) device is inserted into the femoral vein and advanced to an adjacent position in the axillary vein to monitor positioning of the device in the axillary artery. Once the position is confirmed, the device's puncture tool (e.g., sharp stylet or needle-tipped guidewire) can then be passed through the wall of the axillary artery into the axillary vein.

Thereafter, a 6 mm balloon can be placed through the AV puncture (either from the arterial side or the venous side) and inflated to expand the opening. A 6 mm covered stent can then be placed in the expanded opening to maintain the patency of the fistula. Then, to enable retrograde flow of arterial blood from the fistula in the axillary vein down to a peripheral vein in the arm (e.g., cephalic vein, basilic vein or antecubital vein) for hemodialysis access, a valvulotome is inserted into the desired vein to lyse the valves.

In another embodiment, a magnet or magnets on the devices in the axillary vein and axillary artery can be used to line up the fistula puncture point.

Percutaneous Bypass for Femoral-Popliteal Arterial Occlusion

Peripheral artery disease can cause blockage of an artery in the leg, such as the popliteal artery. Current procedures include the use of a grafted bypass leading from the femoral artery to a point beyond the blockage.

Figure 4:
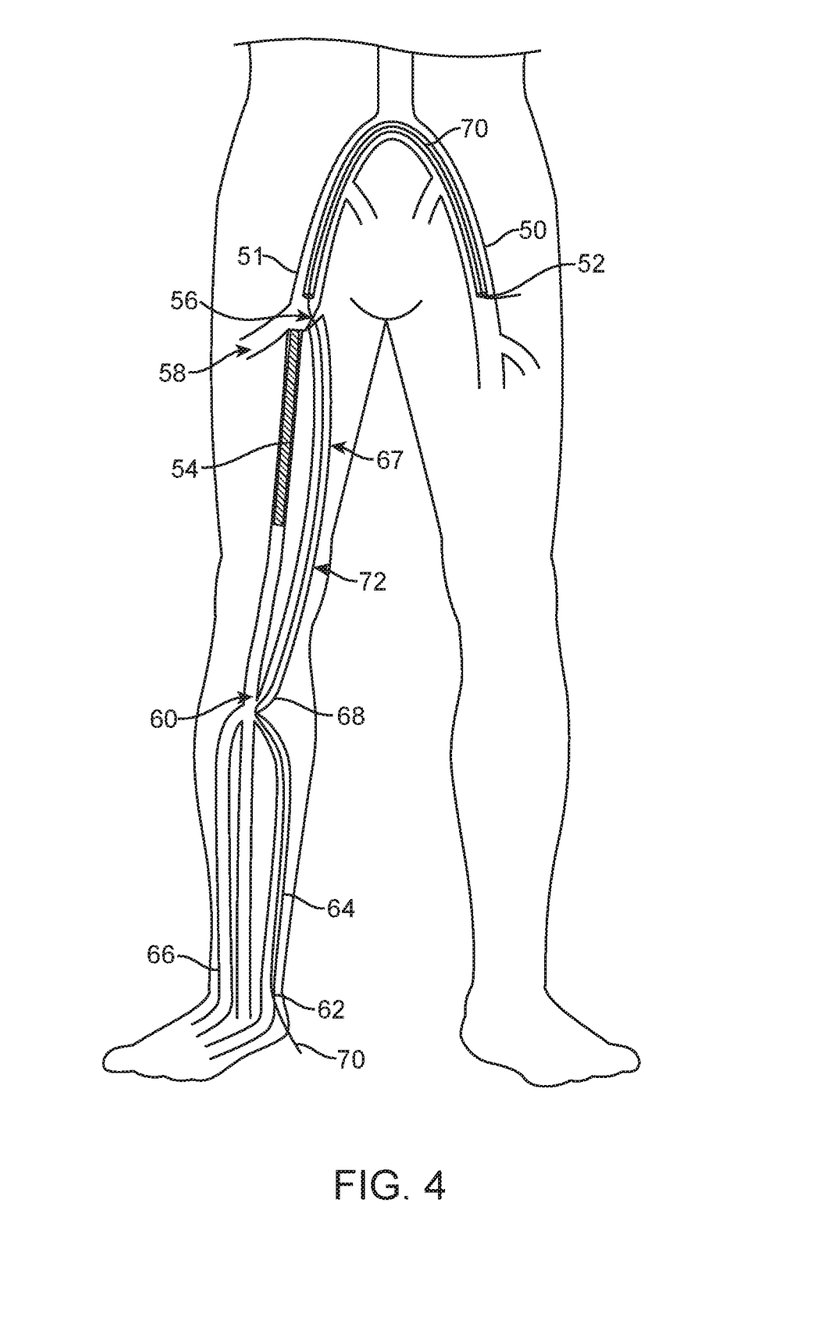
FIG. 4 illustrates placement of a popliteal bypass graft according to an aspect of this invention.

Devices as described in, e.g., U.S. Application No. 61/653,182; U.S. Pat. No. 8,409,236; U.S. application Ser. No. 12/366,517; or U.S. application Ser. No. 11/424,131 can be used to implant a popliteal bypass graft in a less invasive manner. As shown in FIG. 4, to treat a blockage in the patient's right leg, a first device is inserted in a first entry point 52 in the femoral artery 50 in the left leg and advanced through the femoral artery 51 in the right leg to a point just above the blockage 54. In one embodiment, an incision can be made to expose the right femoral artery at the desired exit point 56 (shown here to be near the junction of the profunda femoral artery 58 and the popliteal artery 60), and the device's puncture tool (e.g., sharp stylet or needle-tipped guidewire) can be passed through the femoral artery wall. Alternatively, the device's puncture tool can be passed through the femoral artery wall and skin of the patient at the exit point 56 without first making an incision.

A second device may be inserted at an entry point 62 in the patient's right tibial artery 64 (or, alternatively, the patient's pedal artery 66) and advanced to its desired exit point 68 beyond the blockage point (shown here as near the junction of the popliteal artery and the tibial artery). Once again, an incision can be made to expose the popliteal artery at the exit point 68 prior to passing the device's puncture tool through the arterial wall. Alternatively, the device's puncture tool can be passed through the arterial wall and skin at the exit point 68 without a prior incision.

Next, a subcutaneous tunnel 67 may be formed between two incisions (not shown) at locations 56 and 68. A 260 exchange catheter may be used to facilitate switching of the two guidewires or stylets with a single guidewire 70 extending from entry point 52 to entry point 62 through the subcutaneous tunnel 67. An expandable covered 6 mm stent graft 72 may then be advanced from, e.g., entry point 52 over the guidewire 70 to the subcutaneous tunnel to extend between the femoral artery exit point to the popliteal artery exit point, then expanded to seal the bypass in place.

What is claimed is:

1. A method of placing a central catheter in a peripheral vein in an arm of a patient, the method comprising:
   inserting an access device percutaneously through an entry site in a femoral vein of the patient, the access device comprising a vascular catheter;
   advancing a distal end of the vascular catheter from the entry site to an exit site in the peripheral vein;
   advancing a puncture tool from the distal end of the vascular catheter through the peripheral vein wall and skin of the patient at the exit site;
   after the step of advancing the puncture tool, inserting the central catheter into the peripheral vein at the exit site; and
   inserting a micropuncture catheter into the peripheral vein at the exit site.

2. The method of claim 1, wherein the peripheral vein comprises a cephalic vein.

3. The method of claim 1, wherein the peripheral vein comprises a basilic vein.

4. The method of claim 1, wherein the peripheral vein comprises a brachial vein.

5. The method of claim 1, wherein the puncture tool comprises a sharp stylet.

6. The method of claim 1, wherein the puncture tool comprises a needle-tipped guidewire.

7. The method of claim 1, wherein the inserting the micropuncture catheter into the peripheral vein, comprises advancing the micropuncture catheter over the puncture tool into the peripheral vein.

8. The method of claim 1, further comprising inserting a guidewire into the peripheral vein through the micropuncture catheter.

9. The method of claim 8, further comprising advancing the central catheter over the guidewire into the peripheral vein.

10. The method of claim 1, further comprising advancing the puncture tool from inside the peripheral vein to outside the peripheral vein.

11. The method of claim 1, wherein the exit site comprises a central catheter entry point.

12. A method of placing a peripherally inserted central catheter in a peripheral vein in an arm of a patient, the method comprising:
    inserting an access device percutaneously through an entry site in a femoral vein of the patient, the access device comprising a vascular catheter;
    advancing a distal end of the vascular catheter from the entry site to an exit site in the peripheral vein;
    advancing a puncture tool from the distal end of the vascular catheter through the peripheral vein wall and skin of the patient at the exit site;
    advancing a micropuncture catheter over the puncture tool into the peripheral vein;
    inserting a guidewire into the peripheral vein through the micropuncture catheter; and
    inserting the central catheter into the peripheral vein over the guidewire.

13. The method of claim 12, wherein the peripheral vein comprises a cephalic vein.

14. The method of claim 12, wherein the peripheral vein comprises a basilic vein.

15. The method of claim 12, wherein the peripheral vein comprises a brachial vein.

16. The method of claim 12, wherein the puncture tool comprises a sharp stylet.

17. The method of claim 12, wherein the puncture tool comprises a needle-tipped guidewire.

18. The method of claim 12, further comprising advancing the puncture tool from inside the peripheral vein to outside the peripheral vein.

19. The method of claim 12, wherein the exit site comprises a central catheter entry point.

\* \* \* \* \*